United States Patent [19]

Willi

[11] Patent Number: 5,549,696
[45] Date of Patent: Aug. 27, 1996

[54] INNER SHELL FOR A HIP JOINT SOCKET

[75] Inventor: Roland Willi, Neftenbach, Switzerland

[73] Assignee: Sulzer Medizinaltechnik AG, Winterthur, Switzerland

[21] Appl. No.: 306,053

[22] Filed: Sep. 14, 1994

[30] Foreign Application Priority Data

Nov. 22, 1993 [EP] European Pat. Off. .............. 93810806

[51] Int. Cl.$^6$ ....................................... A61F 2/34
[52] U.S. Cl. ............................................... 623/22
[58] Field of Search ............................. 623/16, 18, 22, 623/23

[56] References Cited

U.S. PATENT DOCUMENTS

| | | | |
|---|---|---|---|
| 4,715,859 | 12/1987 | Shelhas et al. | 623/22 |
| 4,792,337 | 12/1988 | Muller | 623/22 |
| 5,092,897 | 3/1992 | Forte . | |
| 5,360,451 | 11/1994 | Keller | 623/22 |

FOREIGN PATENT DOCUMENTS

| | | | |
|---|---|---|---|
| 0265712 | 5/1988 | European Pat. Off. . | |
| 0313762 | 5/1989 | European Pat. Off. . | |
| 0436317 | 7/1991 | European Pat. Off. . | |
| 0488943 | 6/1992 | European Pat. Off. . | |
| 0586335 | 3/1994 | European Pat. Off. | 623/22 |
| 3331191 | 4/1985 | Germany . | |
| 3533432 | 3/1987 | Germany . | |
| 0677072 | 4/1991 | Switzerland | 623/22 |

WO93/16662 9/1993 WIPO .

*Primary Examiner*—David H. Willse
*Assistant Examiner*—Bruce E. Snow
*Attorney, Agent, or Firm*—Townsend and Townsend and Crew

[57] ABSTRACT

The metallic inner shell (1) is guidable into the inner hollow volume of an outer shell (2) and fastenable to the outer shell (2) with the fastening element (8). A two-part hip joint socket (3) is thus produced. To achieve this, support regions of the inner shell (1) are approximately positioned into a groove (11) of the outer shell (2) and, from there, the inner shell (1) is moved into the outer shell (2) via a pivotal movement so that the support regions completely seat into the groove (11) and the fastening element (8) adopts the position shown. The intermediate volume between the inner shell (1) and the outer shell (2) thus narrows in the direction of taper (13) so that the fastening element (8), when tightened in the direction (13), wedges itself with its head (9) between the boundary surface (1i) of the inner shell (1) and the groove (11) of the outer shell (2). Play between the inner thread (7a) and the outer thread (8a) is preferably provided so that, when the fastening element (8) is tightened, the force transmission region (9b) of the head (9) seats against the boundary surface (1i) of the inner shell (1) and the force transmission region (9a) seats against the groove (11) of the outer shell (2). The inner shell (1) thus lies wedged in the outer shell (2) due to the fact that the fastening element (8) transmits a radially oriented force between the inner shell (1) and the outer shell (2).

14 Claims, 4 Drawing Sheets

(B-B)

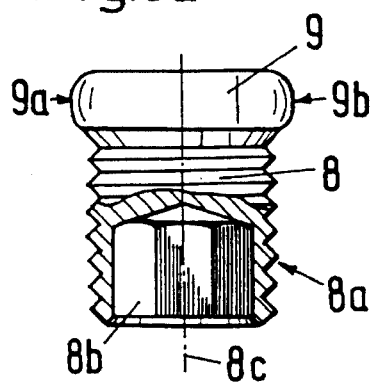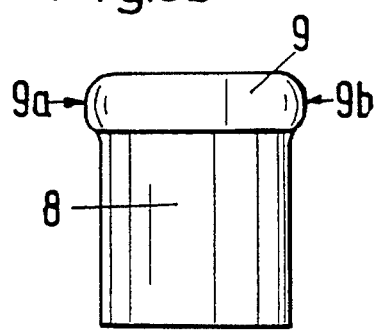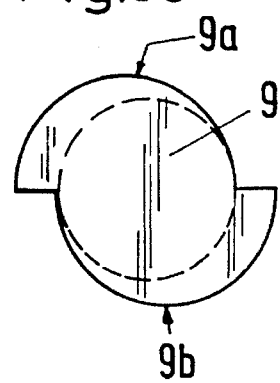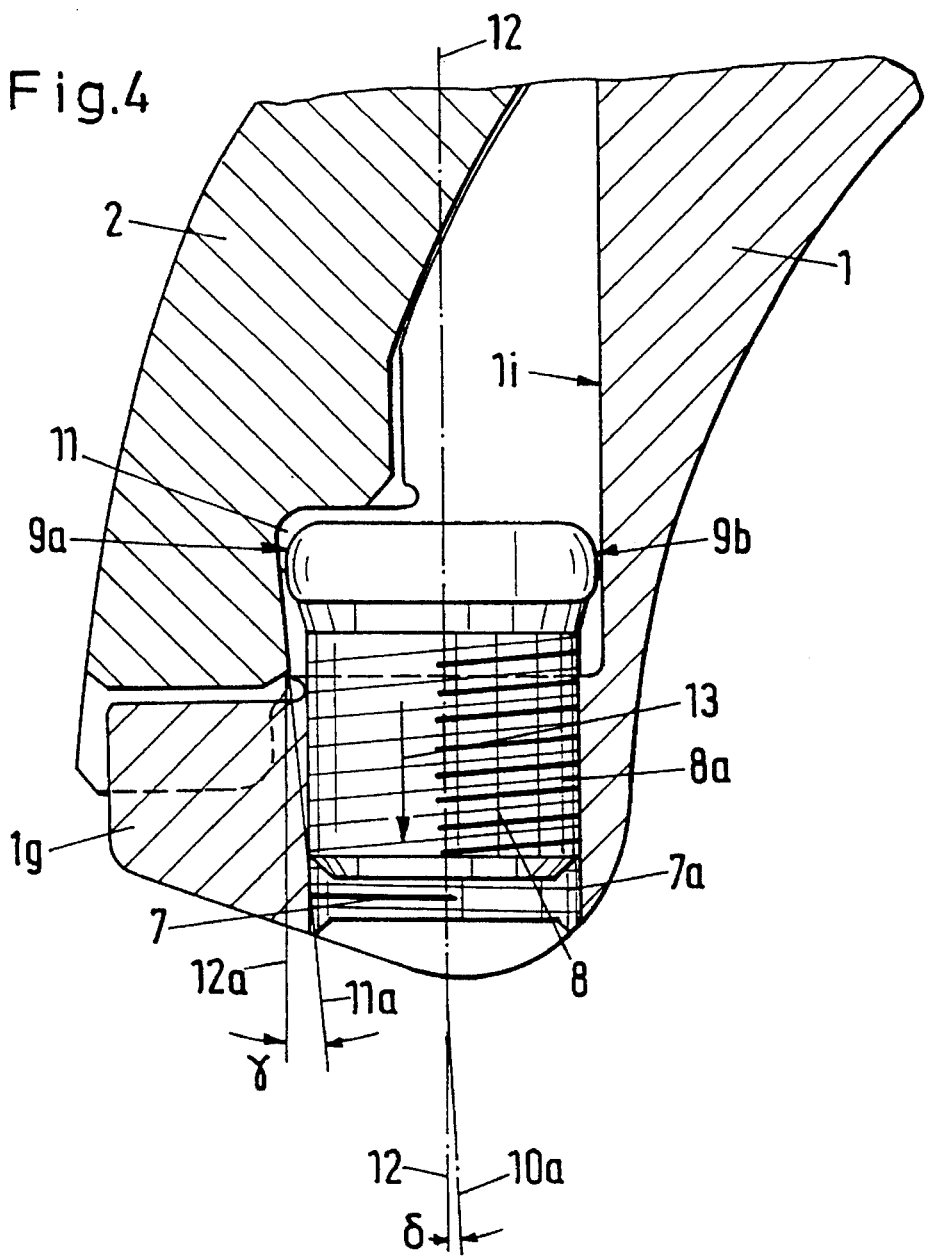

5,549,696

INNER SHELL FOR A HIP JOINT SOCKET

BACKGROUND OF THE INVENTION

The invention relates to an inner shell for an artificial hip joint socket. The invention further relates to a hip joint socket with an inner shell and to a method which allows the inner shell to be combined with a known outer shell to form a hip joint socket.

Artificial hip joint sockets often have a two-part construction; an anchoring body or outer shell which is fixable in the bone, and a socket body or inner shell for the receipt of the head of the joint.

For instance, European publication EP 0 313 762 A1 discloses an anchoring body in the form of a hemispherical shell which is fixable in the pelvis with the aid of bone screws and which also comprises a socket body with a joint shell in which the head of the joint seats. The socket body, which is made from plastic, is fixable in the anchoring body by means of a snap seal. Plastic socket bodies have the advantage that they are able to form the cushioning member of a snap connection due to the high elasticity of the plastic. However, they have the disadvantage that the socket shell wears down over the long term due to the effects of the head of the joint so that during a re-operation it may be necessary to replace the socket body or the entire hip joint socket.

SUMMARY OF THE INVENTION

It is therefore an object of the invention to form an inner shell with reduced wear properties which may also be fitted into an existing anchoring body originally made to receive a plastic inner shell.

This is accomplished in accordance with the present invention by an inner shell for placement in a metal outer shell of an acetabular socket implant, which, for example, may already be affixed to a bone. The outer shell has a concave inner surface which terminates at a large opening of and defines a groove with a radially inwardly oriented surface which, for example, may be part of a snap-in fastener for an insert made of a plastic material.

The inner shell is a generally hemispherical metal shell with an open base, a pole opposite the base, an axis extending from the base to the pole, a concave interior surface, a convex exterior surface, and a shape for placing the inner shell into the outer shell with play so that the inner shell can move relative to the outer shell when disposed therein. The inner shell further includes first and second, spaced-apart support regions proximate the base which project radially outwardly from the outer surface and which are positioned to be located in the groove when the inner shell is placed inside the outer shell. An aperture is located proximate the base and extends from a side of the base facing away from the pole to the exterior surface of the inner shell at an angle with respect to the axis. The aperture is positioned so that one end of it on the exterior surface at least partially overlies the inwardly oriented surface of the groove. A fastening element is axially movably disposed in and engages the aperture and includes a portion, such as a head, positioned beyond the exterior surface of the inner shell which contacts the radially inwardly oriented surface of the groove. The head can be tightened against the inwardly oriented surface of the groove to press the head and the support regions into engagement with the inwardly oriented surface of the groove and thereby secure the inner shell to the outer shell.

A metallic inner shell made in accordance with the invention can be fitted into an existing anchoring body or an existing outer shell. The inner shell of the invention has the advantage that, during a re-operation, the plastic inner shell is replaceable with a metal inner shell in such a manner that the in-grown outer shell remains in place. The wear of the inner shell is thus reduced in a manner which is protective of the bone tissue. Existing metallic outer shells are manufactured with the rough tolerances in the region of the snap connection usual for plastic inner shells. A further advantage of the invention is that outer shells, in particular existing ones, can be fitted with a metal or a plastic inner shell, according to choice.

BRIEF DESCRIPTION OF THE DRAWINGS

FIG. 1b is a cross-sectional side view of the metallic inner shell and is taken on line B—B of FIG. 1a;

FIG. 3a is a side view of a fastening element shown partially in section;

FIG. 3b is a side view of a further fastening element;

FIG. 3c is a plan view onto the head of a further fastening element;

FIG. 4 is a detail of a partial section through a hip joint socket, the inner and outer shells of which being held together by a fastening element;

DETAILED DESCRIPTION OF THE PREFERRED EMBODIMENTS

Figure 2A:
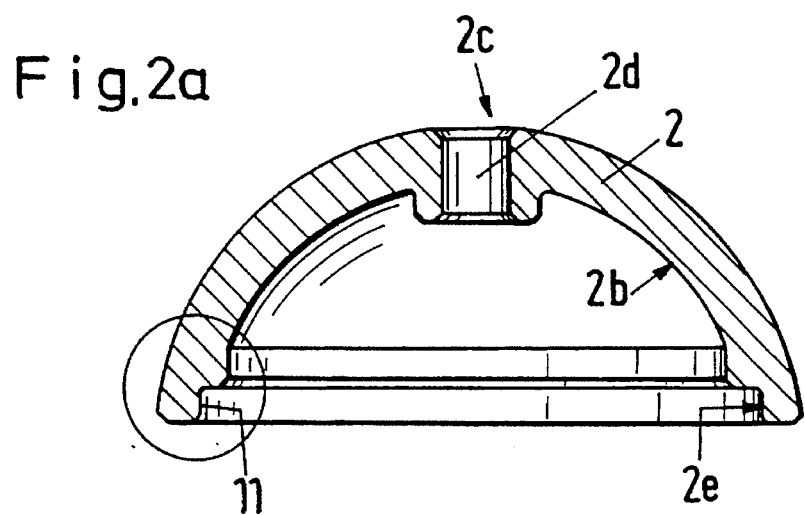
FIG. 2a is a cross-sectional view through a metallic outer shell.
Figure 2B:
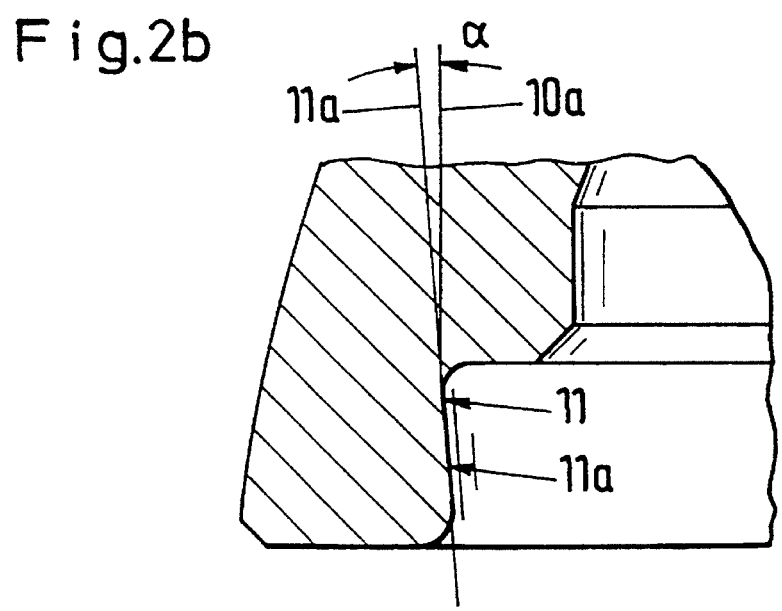
FIG. 2b shows a portion of a groove of the outer shell.

An example of a known metallic outer shell 2 as used for two-part hip joint sockets is shown in FIG. 2a. The outer shell 2 shown has a recess 2d in the pole region 2c and also a groove 11 along the equatorial circumference 2e on the inner surface 2b. The section of FIG. 2a depicted in FIG. 2b shows the groove 11 which has a boundary surface 11a formed by the equatorial circumference 2e and which is inclined at an angle alpha relative to a vertical 10 in such a way that the diameter of the groove 11 enlarges corresponding to the angle alpha as one moves towards the pole region 2c. It is known, for example from EP 0 313 762, to employ a plastic inner shell 1 with an outer shell 2 of such a design. For this, the inner shell 1 has a ring-shaped projection 1h on its outer surface 1a which snaps into the groove 11 in the inner hollow volume of the outer shell 2 so that the inner shell 1 is fixed in the outer shell 2.

Figure 1A:
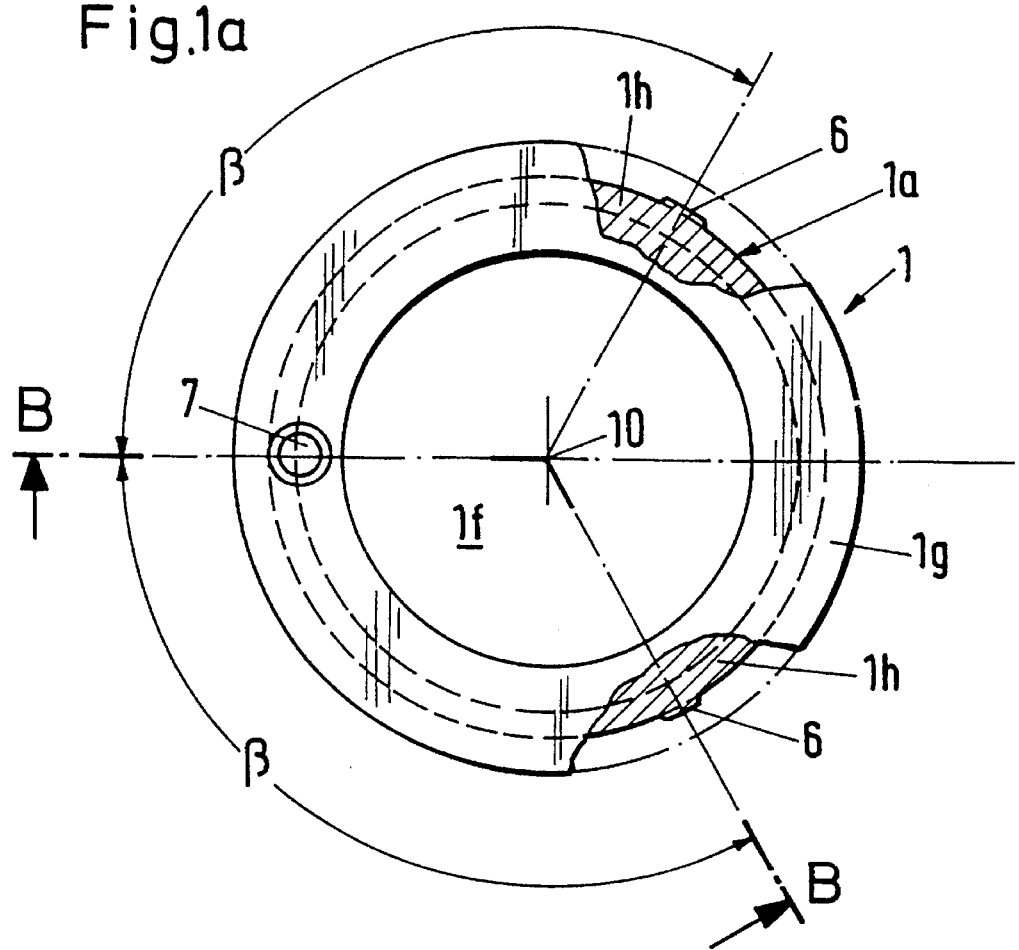
FIG. 1a is a view from below of a metallic inner shell.

FIG. 1a is a view from below of a metallic inner shell 1 made in accordance with the invention which comprises an inner hollow volume 1f, a projection 1g and an outer surface 1a. Further, the axial direction 10 extending through the pole 4 of the inner shell 1 is shown, this direction extending vertical to the shown plane of view. The projection 1g is perforated at one point by an aperture 7, for instance a bore. Further, the inner shell comprises at least two support regions 6 on its outer surface 1a, preferably in the region of the equator, these support regions projecting slightly from the outer surface 1a. In the embodiment shown, there are two support regions 6 which, with reference to a connecting line between the axial direction 10 and the aperture 7, are each displaced by an angle beta and disposed at the outer surface 1a in the region of the equator.

Figure 1B:
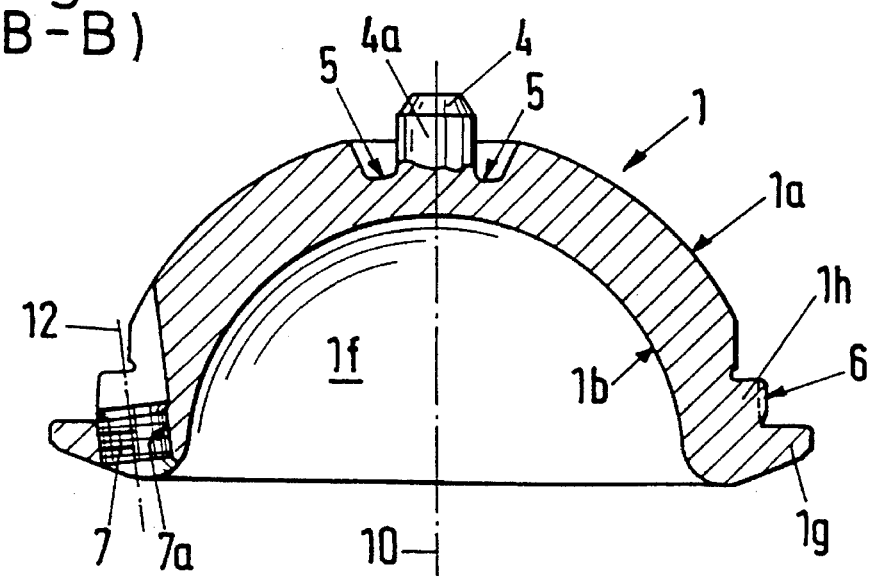

FIG. 1b shows the inner shell with outer surface 1a, inner surface 1b, the inner hollow volume 1f as well as the projection 1g. The axial direction 10 extends through the pole 4 of the inner shell 1, wherein the pole 4 in the present embodiment is formed as a centering spigot 4a which rises out of and is surrounded by a support region 5. Further, the direction of axis 12 of aperture 7 is visible. In the illustrated embodiment, the aperture has an internal thread 7a. Further, the projection 1h of the inner shell 1, which extends about the outer surface 1a in the region of the equator, is visible. A support region 6 is arranged at the projection 1h in such a way that support region 6 extends radially relative to the axial direction 10 slightly beyond the projection 1h.

Figure 1C:
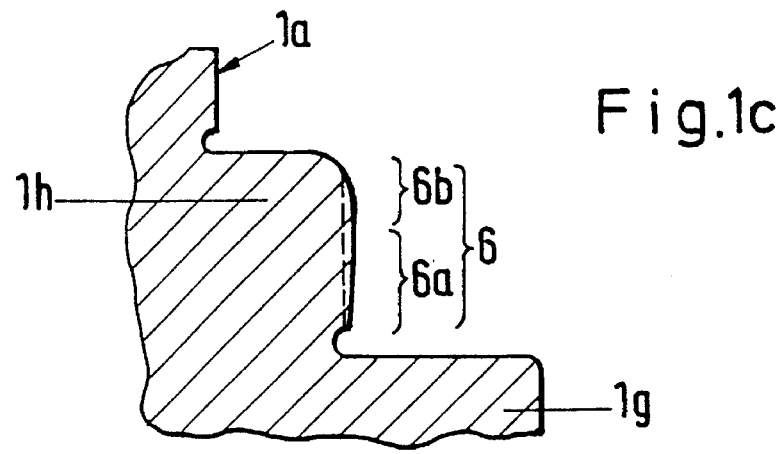
FIG. 1c shows a portion of a support region of the inner shell.

FIG. 1c shows the support region 6 disposed in the region of the projection 1h in detail. The region extends radially, relative to the axial direction 10, and can have a variety of configurations. In the illustrated embodiment, the support region 6 has a widening region 6a within which the outer diameter of the support region 6 increases towards the pole 4. The widening region 6a blends smoothly into a narrowing region 6b within which the outer diameter of the support region 6 decreases towards the pole 4. The height of the support region 6 in the axial direction 10 is limited by the height of the projection 1h.

FIG. 3a shows a fastening element 8 which serves to releasably fasten the inner shell 1 in the outer shell 2. The cylindrical fastening element 8 comprises an outer thread 8a on its lateral surface, a recess 8b for engagement with a fastener tool on one of its end faces and, on its other end face, a head 9 which has a diameter larger than that of the outer thread 8a. The head 9 comprises force transmission regions 9a and 9b extending parallel to the axial direction 8c of the fastening element 8 which serve to transmit forces acting onto the head 9, especially forces radial to the axial direction 8c. In comparison to the embodiment of FIG. 3a, the fastening element 8 shown in FIG. 3b does not have an outer thread 8a, which is why the fastening element 8 is suitable for being knocked or hammered in. In FIG. 3c, a further embodiment shows a plan view onto a head 9 which comprises two continuously enlarging force transmission regions 9a and 9b. The fastening element 8 and the head 9 may also be made separately, for instance in such a manner that the head 9 is rotatably mounted in the fastening element 8. The head 9 could thus also have a rectangular or square shape as viewed from above.

Figure 5:
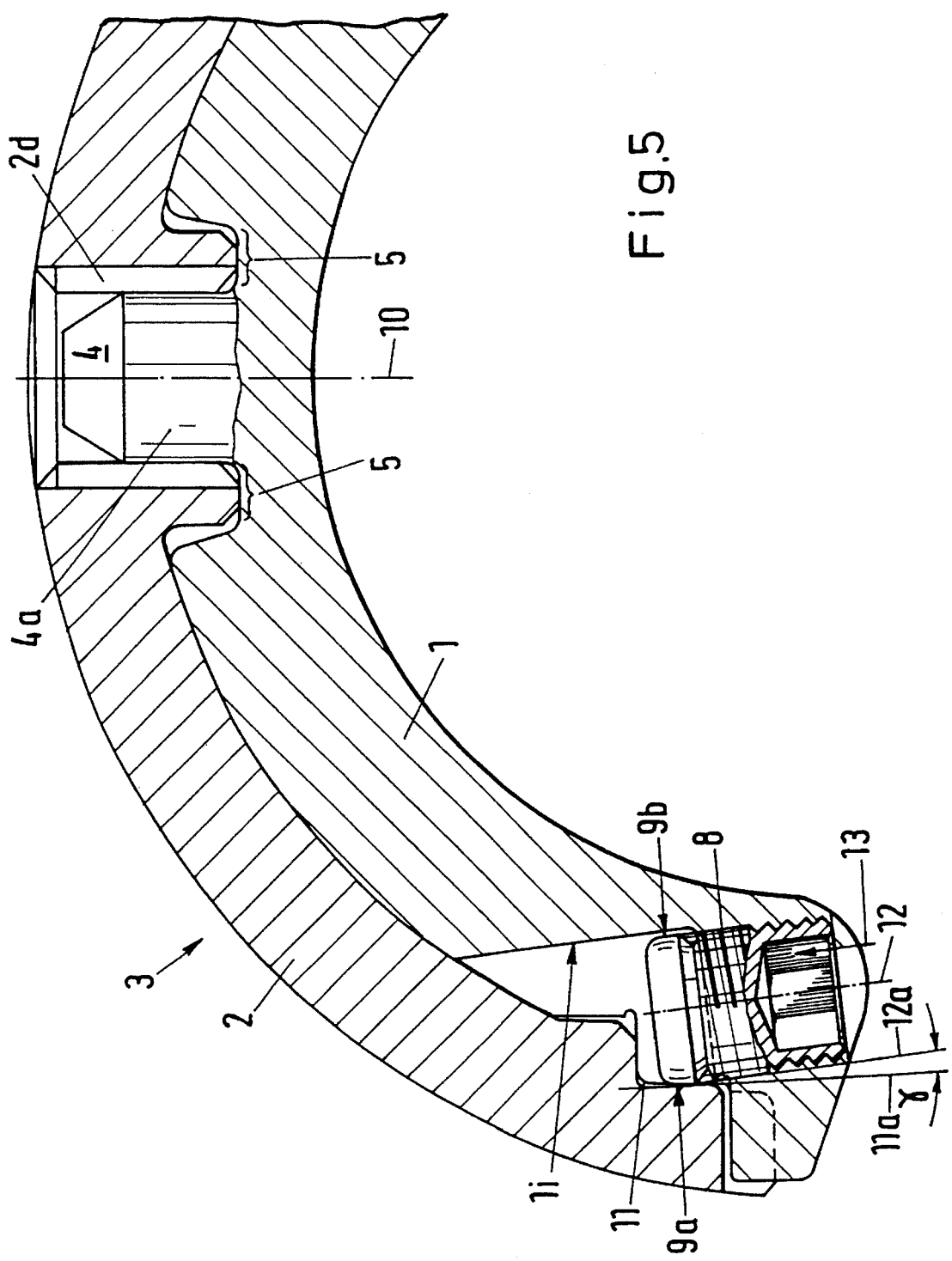
FIG. 5 is a partial section through a hip joint socket with inner and outer shells and shows a further fastening arrangement.

The inner shell 1 of the invention is insertable into the inner hollow volume of an outer shell 2 and fastenable to the outer shell 2 by the fastening element 8. To do this, the supporting regions 6 of the inner shell 1 are approximately inserted into the groove 11 of the outer shell 2 and, from there, the inner shell 1 is moved into the outer shell 2 via a pivotal movement so that the support regions 6 seat fully into the groove 11 and so that the fastening element 8 adopts a position as shown in FIG. 4 or FIG. 5. The section depicted in FIG. 4 shows the inner shell 1 lying in the outer shell 2. The fastening element 8, which comprises an outer thread 8a, has been screwed into the aperture 7 of the inner shell 1 prior to the pivotal movement. For this, the geometry of the groove 11, the pivotal point of the inner shell 1 defined by the support regions 6, and also the design and position of the fastening element 8 are chosen in such a way that the inner shell 1 is able to pivot into the outer shell 2 when the position of the fastening element 8 is as shown. In the illustrated embodiment, the axis 12 of the aperture 7 deviates from a line 10a which is parallel to the axial direction 10 by an angle delta which may amount to up to a few degrees. Further, an angle gamma is formed between the direction of extension 11a of the groove 11 and a line 12a that is parallel to axis 12. The angle gamma ensures that the intermediate volume between the inner shell 1 and the outer shell 2 narrows in the direction of taper 13 so that, when tightened in the direction 13, the fastening element 8 wedges itself with the head 9 between inner shell 1 and outer shell 2. Play between the inner thread 7a and the outer thread 8a is preferably provided so that, when the fastening element 8 is tightened, the force transmission region 9b seats onto a boundary surface 1i of the inner shell 1 and the force transmission region 9a seats in groove 11 of the outer shell 2. The inner shell 1 thus lies wedged in the outer shell 2 due to the fact the fastening element 8 exerts a radially oriented force relative to the axis direction 10, between the inner shell 1 and the outer shell 2, and due to the fact that the fastening element 8 presses the inner shell 1 in the direction of axis 12 into the outer shell 2.

At least three effective connections between the two shells are necessary for a reliable wedging of the inner shell in the outer shell 2. In FIG. 1a, the three effective connections (two support regions 6 as well as a fastening element 8 at the position of the aperture 7) are distributed uniformly over the circumference. The effective connections could also be distributed along the circumference differently. In particular, more than two support regions 6 can be arranged along the circumference, or one support region 6 can be combined with two or more fastening elements 8, or three or more fastening elements 8 can be provided.

FIG. 5 shows a further arrangement of the fastening element 8 between the inner shell 1 and the outer shell 2. An angle gamma exists between the direction of line 12a of the aperture 7 and the direction of extension 11a of the groove 11. The angle between the axial direction 10 and the aperture axis 12 is larger than the angle between the axial direction 10 and a lateral surface 11a of the groove 11 of the outer shell 2. The intermediate volume between inner shell 1 and outer shell 2 narrows in the direction of taper 13 so that the fastening element 8, when tightened in the direction 13, wedges itself with its head 9 between the boundary surface 1i of the inner shell 1 and the groove 11 of the outer shell 2. Play between the internal thread 7a and the outer thread 8a is therefore preferably provided so that, when the fastening element 8 is tightened, the force transmission region 9b seats against boundary surface 1i of the inner shell 1, and the force transmission region 9a seats against the groove 11 of the outer shell 2. The inner shell 1 thus lies wedged in the outer shell 2 due to the fact that the fastening element 8 transmits a radial force (relative to the axial direction 10) between the inner shell 1 and the outer shell 2.

FIG. 5 shows further that the inner shell 1 can be guided in a recess 2d of the outer shell by a cylindrical protuberance 4a at the pole 4 and that the inner shell 1 can comprise a support region 5 in the region of the pole 4 to establish an effective connection between inner shell 1 and outer shell 2 at the region of the pole.

In the arrangement of FIG. 5, the angle gamma, as well as the shape of the head 9, can be chosen so that the spacing between inner shell 1 and outer shell 2 in the region of the aperture 7 is continuously adjustable. In the embodiment shown in FIG. 5, the inner and outer shells lie on top of one another. If the fastening element 8 is screwed in deeply in the taper direction 13, the spacing between inner shell and outer shell increases independently of the angle gamma and the nature of the surface of the outer shell 2 and head 9, thereby rendering it adjustable.

A fastening element 8 made according to FIG. 3b can be similarly used in the arrangement of FIG. 5 by not providing the aperture 7 with an inner thread 7a so that the fastening element 8 can be knocked or hammered in between the inner shell 1 and the outer shell 2 like a nail until the force transmission regions 9a and 9b wedge themselves in the intermediate volume which is itself tapered. For this, the head 9 can have approximately the same diameter as the fastening element 8 so that the fastening element 8 is insertable into the aperture 7 after shells 1 and 2 have been fitted together.

The fastening element 8 can have a variety of configurations for effecting a wedging between inner shell 1 and outer shell 2. Consequently, the embodiment of a head 9 of a fastening element 8 shown in FIG. 3c should be regarded as only one example from a large number of possible forms which press the force transmission regions 9a and 9b against the inner shell 1 and the outer shell 2 respectively via a pivotal movement of the fastening element 8 to wedge the inner shell 1 in the outer shell 2.

What is claimed is:

1. An inner shell for an acetabular socket implant including a metal outer shell adapted to be affixed to a bone having a concave inner surface terminating at a large opening of the outer shell and a groove defined by the inner surface, the inner shell comprising: a generally hemispherical metal shell having an open base, a pole opposite the base, and an axial direction from the base to the pole, first and second, spaced-apart support regions projecting radially past an outer surface of the inner shell so that upon placement of the inner shell in the outer shell the support regions engage the groove in the outer shell, the inner shell further including an aperture proximate the base having an axis and an internal thread; and a fastening element for placement in the aperture having an external thread cooperating with the internal thread of the aperture so that the fastening element is movable relative to the aperture so that, upon placement of the inner shell in the outer shell, the fastening element can be moved relative to the aperture into engagement with the inner surface of the outer shell in a manner generating a force acting transversely to the axial direction and biasing the support regions against a surface of the groove in the outer shell to thereby secure the inner shell to the outer shell.

2. An inner shell according to claim 1 including an additional support region on the outer surface located in a vicinity of the pole of the inner shell.

3. An inner shell according to claim 2 including a cylindrical protuberance projecting from the outer surface at the pole and extending in the axial direction.

4. An inner shell according to claim 1 wherein the fastening element and the aperture have cooperating, smooth surfaces.

5. An inner shell according to claim 1 wherein the groove has a radially inwardly facing surface which has a taper which diverges in the axial direction and defines a first angle relative to the axial direction, wherein the aperture axis is angularly inclined with respect to the axial direction and defines a second angle relative to the axial direction, wherein the second angle is larger than the first angle, and wherein the aperture is further positioned so that the fastening element, when moved along the aperture towards the outer shell, engages the radially inwardly facing surface of the groove.

6. An inner shell according to claim 1 wherein the groove has a radially inwardly facing surface which has a taper which diverges in the axial direction and defines a first angle relative to the axial direction, wherein the aperture axis is angularly inclined with respect to the axial direction and defines a second angle relative to the axial direction, wherein the second angle is smaller than the first angle, and wherein the aperture is further positioned so that the fastening element, when moved along the aperture away from the outer shell, engages the radially inwardly facing surface of the groove.

7. An inner shell according to claim 1 wherein the fastening element includes a head and wherein there is play between the fastening element and the aperture so that the head can move laterally with respect to the aperture whereby, upon insertion of the inner shell in the outer shell and a tightening of the fastening element, the head can move laterally to form a connection between a radially inwardly facing surface of the groove in the outer shell and the outer surface of the inner shell.

8. An inner shell for an acetabular socket implant including a metal outer shell adapted to be affixed to a bone having a concave inner surface terminating at a large opening of the outer shell and defining a groove proximate the large opening with a radially inwardly oriented surface, the inner shell comprising: a generally hemispherical metal shell having an open base, a pole opposite the base, an axis extending from the base to the pole, a concave interior surface, a convex exterior surface, and a shape for placing the inner shell into the outer shell with play so that the inner shell can move relative to the outer shell when disposed therein, the inner shell further including first and second, spaced-apart support regions proximate the base, projecting radially outwardly from the outer surface and positioned to be located in the groove when the inner shell is placed inside the outer shell, and an aperture located proximate the base and extending from a side of the base facing away from the pole to the exterior surface of the inner shell at an angle with respect to the axis and which is positioned so that an end of the aperture on the exterior surface at least partially overlies the inwardly oriented surface of the groove when the inner shell is placed inside the outer shell; a fastening element axially movably disposed in and engaging the aperture and including a portion positioned beyond the exterior surface of the inner shell for contacting the radially inwardly oriented surface of the groove; and means defined by the inner shell and the fastening element for tightening the portion against the inwardly oriented surface of the groove when the inner shell is disposed in the outer shell to thereby press the portion and the support regions into engagement with the inwardly oriented surface of the groove and thereby secure the inner shell to the outer shell.

9. An inner shell according to claim 8 wherein the radially inwardly oriented surface of the groove has a taper which diverges in a direction from the base towards the pole of the outer shell, and wherein the portion of the fastening means and the support regions are positioned so that they engage a part of the radially inwardly oriented surface which is spaced from the large opening to form a wedge connection between the inner shell and the outer shell when the fastening means is tightened.

10. An inner shell for placement in a metal outer shell of an acetabular socket implant affixed to a bone having a concave inner surface terminating at a large opening of the outer shell and defining a groove proximate the large opening with a radially inwardly oriented surface forming part of a snap-in fastener for an insert made of a plastic material, the inner shell comprising: a generally hemispherical metal shell having an open base, a pole opposite the base, an axis extending from the base to the pole, a concave interior surface, a convex exterior surface, and a shape for placing the inner shell into the outer shell with play so that the inner shell can move relative to the outer shell when disposed therein, the inner shell further including first and second, spaced-apart support regions proximate the base, projecting radially outwardly from the outer surface and positioned to be located in the groove when the inner shell is placed inside the outer shell, and an aperture located proximate the base and extending from a side of the base facing away from the pole to the exterior surface of the inner shell at an angle with respect to the axis and which is positioned so that an end of the aperture on the exterior surface at least partially overlies the inwardly oriented surface of the groove when the inner shell is placed inside the outer shell; a fastening element axially movably disposed in and engaging the aperture and including a portion positioned beyond the exterior surface of the inner shell for contacting the radially inwardly oriented surface of the groove; and means defined by the inner shell and the fastening element for tightening the portion against the inwardly oriented surface of the groove when the inner shell is disposed in the outer shell to thereby press the portion and the support regions into engagement with the inwardly oriented surface of the groove and thereby secure the inner shell to the outer shell.

11. An inner shell for an acetabular socket implant including a metal outer shell adapted to be affixed to a bone having a concave inner surface terminating at a large opening of the outer shell and a groove defined by the inner surface, the groove having a radially inwardly facing surface which has a taper which diverges in the axial direction and defines a first angle relative to the axial direction, the inner shell comprising: a generally hemispherical metal shell having an open base, a pole opposite the base, and an axial direction from the base to the pole, first and second, spaced-apart support regions projecting radially past an outer surface of the inner shell so that upon placement of the inner shell in the outer shell the support regions engage the groove in the outer shell, the inner shell further including an aperture proximate the base having an axis; and a fastening element for placement in and engaging the aperture shaped and movable relative to the aperture so that, upon placement of the inner shell in the outer shell, the fastening element can be moved relative to the aperture into engagement with the inner surface of the outer shell in a manner generating a force acting transversely to the axial direction and biasing the support regions against a surface of the groove in the outer shell to thereby secure the inner shell to the outer shell; wherein the aperture axis is angularly inclined with respect to the axial direction and defines a second angle relative to the axial direction, wherein the second angle is larger than the first angle, and wherein the aperture is further positioned so that the fastening element, when moved along the aperture towards the outer shell, engages the radially inwardly facing surface of the groove.

12. An inner shell according to claim 2 wherein the fastening element includes an external thread and the aperture includes an internal thread formed to cooperate with the external thread.

13. An inner shell for an acetabular socket implant including a metal outer shell adapted to be affixed to a bone having a concave inner surface terminating at a large opening of the outer shell and a groove defined by the inner surface, the groove having a radially inwardly facing surface which has a taper which diverges in the axial direction and defines a first angle relative to the axial direction, the inner shell comprising: a generally hemispherical metal shell having an open base, a pole opposite the base, and an axial direction from the base to the pole, first and second, spaced-apart support regions projecting radially past an outer surface of the inner shell so that upon placement of the inner shell in the outer shell the support regions engage the groove in the outer shell, the inner shell further including an aperture proximate the base having an axis; and a fastening element for placement in and engaging the aperture shaped and movable relative to the aperture so that, upon placement of the inner shell in the outer shell, the fastening element can be moved relative to the aperture into engagement with the inner surface of the outer shell in a manner generating a force acting transversely to the axial direction and biasing the support regions against a surface of the groove in the outer shell to thereby secure the inner shell to the outer shell; wherein the aperture axis is angularly inclined with respect to the axial direction and defines a second angle relative to the axial direction, wherein the second angle is smaller than the first angle, and wherein the aperture is further positioned so that the fastening element, when moved along the aperture away from the outer shell, engages the radially inwardly facing surface of the groove.

14. An inner shell for an acetabular socket implant including a metal outer shell adapted to be affixed to a bone having a concave inner surface terminating at a large opening of the outer shell and a groove defined by the inner surface and including a radially inwardly facing surface, the inner shell comprising: a generally hemispherical metal shell having an open base, a pole opposite the base, and an axial direction from the base to the pole, first and second, spaced-apart support regions projecting radially past an outer surface of the inner shell so that upon placement of the inner shell in the outer shell the support regions engage the groove in the outer shell, the inner shell further including an aperture proximate the base having an axis; and a fastening element for placement in and engaging the aperture shaped and movable relative to the aperture so that, upon placement of the inner shell in the outer shell, the fastening element can be moved relative to the aperture into engagement with the inner surface of the outer shell in a manner generating a force acting transversely to the axial direction and biasing the support regions against a surface of the groove in the outer shell to thereby secure the inner shell to the outer shell; wherein the fastening element includes a head and wherein there is play between the fastening element and the aperture so that the head can move laterally with respect to the aperture whereby, upon insertion of the inner shell in the outer shell and a tightening of the fastening element, the head can move laterally to form a connection between the radially inwardly facing surface of the groove in the outer shell and the outer surface of the inner shell.

\* \* \* \* \*